United States Patent [19]
Dickson et al.

[11] Patent Number: 6,077,938
[45] Date of Patent: Jun. 20, 2000

[54] MONOCLONAL ANTIBODY TO AN 80 KDA PROTEASE

[75] Inventors: Robert B. Dickson, Silver spring, Md.; Chen-Yong Lin, Falls Church, Va.

[73] Assignee: Georgetown University, Washington, D.C.

[21] Appl. No.: 08/957,816

[22] Filed: Oct. 27, 1997

Related U.S. Application Data

[60] Provisional application No. 60/029,037, Oct. 28, 1996.
[51] Int. Cl.[7] .................................................. C07K 16/00
[52] U.S. Cl. .................. 530/388.26; 530/387.1; 530/387.7; 530/388.1; 530/388.8; 436/64; 435/287.2
[58] Field of Search ............................... 530/387.1, 387.7, 530/388.1, 388.26, 388.8; 436/64; 435/287.2

[56] References Cited

PUBLICATIONS

Lin et al., Characterization of a Novel, Membrane–bound, 80–kDa Matrix–degrading Protease from Human Breast Cancer Cells, J. Biol. Chem., 272(14): 9147–9152, (Apr. 14, 1997).

*Primary Examiner*—Laurie Scheiner
*Attorney, Agent, or Firm*—Burns, Doane, Swecker & Mathis, LLP

[57] ABSTRACT

Compositions of the instant invention comprise a monoclonal antibody designated as 21-9 which binds selectively with an 80 kDa matrix-degrading proteinase having an average molecular weight of about 80 kDa, which is active in the presence of $Ca^2$, $Mg^{2+}$ and $Mn^{2+}$.

9 Claims, No Drawings

MONOCLONAL ANTIBODY TO AN 80 KDA PROTEASE

This application takes priority from Provisional Patent Application 60/029,037 filed Oct. 28, 1996.

FIELD OF THE INVENTION

This invention relates to use of monoclonal antibodies as a means of identifying a 80 kDa protease in a tissue samples.

BACKGROUND OF THE INVENTION

U.S. Pat. No. 5,482,848 to Dickson, et al., which is incorporated herein be reference in its entirety, discloses and claims an 80 kDa metalloproteinase and antibodies useful for evaluating and treating breast cancer. The protease had been isolated from hormone-dependent, but not from hormone independent, breast cancer cells.

The capacity of cancer cells to metastasize and invade tissue is facilitated by degradation of the basement membrane (BM). Several protease enzymes have been shown to facilitate the process of invasion of tumor cells. One family of enzymes known as matrix metalloproteinases (MMP) has been implicated as enhancing the degradation of the basement membrane to allow tumorous cells to invade tissues. MMP's differ in molecular weight and in their antigenic properties. Previously, two major metalloproteinases studied having molecular weights of about 70 kDa and 92 kDa. Both of these MMP's have been shown to enhance ability of tumor cells to metastasize. Two natural inhibitors of these enzymes known as tissue inhibitors of metalloproteinase (TIMP) have been identified. The inactivated, unclipped collagenases are generally secreted as a complex with TIMP. Enzymic activity of the 72 kDa and 92 kDa depends on secreted ratios of collagenase/TIMP and the activational process. Methods of measuring 72 kDA and 92 kDa collagenase breast cancer are being used to develop useful prognostic indicators.

Fully metastatic models of hormone-responsive breast cancer have only recently been described, and some progress has been made in studying in vitro invasion systems to evaluate regulatory mechanisms. The reconstituted basement membrane extract, Matrigel, has been utilized in assessing invasive potential of cancer cells. Invasion of hormone-dependent breast cancer cells in vitro is stimulated by estrogen or tamoxifin (a weakly estrogenic, nonsteroidal antiestrogen) but not by the steroidal pure antiestrogen ICI 164,384.

Recently a synthetic low-molecular-weight MMP inhibitor, [4-(N-hydroxyamino)-2R-isobutyl-3S-(thiopen-2-ylthiomethyl)-succinyl]-L-phenylalanine-N-methylamide (BB-94) has been identified which has been shown to be effective in treatment of ovarian malignancies and in some forms of breast cancer. That agent seems to be effective against both the 72 kDa and 92 kDa metalloproteinases.

U.S. Pat. No. 5,482,848 describes a matrix-degrading protease having a molecular weight of about 80 kDa which is present in hormone-dependent human breast cancer cells. The enzyme is active in the presence of calcium, manganese or magnesium ions.

DETAILED DESCRIPTION OF THE INVENTION

Because degradation of the extracellular matrix (ECM) (basement membrane and interstitial stroma) is an important aspect of metastasis, and is required for metastatic cancer cells to migrate through anatomical barriers and to invade tissues, the ability to evaluate the extent and location of factors which facilitate metastasis is important in evaluation of any malignant tumor. It was previously known that the presence of the 80 kDa proteinase may be detected directly by analysis of tumor tissue or indirectly by immunological means. However, it was not previously known that the 80 kDa protein was present around the periphery of the cells. Expression of this novel, integral membrane gelatinase could allow breast cancer cells an alternative to other previously described matrix-degrading enzymes for degradation of the ECM in close proximity to their surfaces. The discovery of the monoclonal antibody used in accord with the methods of the invention facilitate characterization of the tumor. Using the methods of the invention enables the pathologist and the oncologist to more effectively plan the treatment of the patient.

While the 80 kDa protein was originally found in the breast tissue, it has now been found to be present in other malignant cells from gynecological tumors. Expression of the protease was negligible in non-cancerous breast and stomal tissues. Among ovarian tumors, the protease was detected in nine out of ten primary malignancies, including one mucinous cystadenocarcinoma, three serous cystadenocarcinomas, five endometrioid carcinomas and one clear cell carcinoma. The protease was also detected in two ovarian adenocarcinoma metastases from colon and breat primary tumors. The expression of the protease was negligible or undetected in an unclassifiable ovarian carcinoma, a mucinous tumor of low malignant potential and sex cord/stomal tumors, including two fibrothecomas and one granulosa cell tumor. Among uterine tumors, the protease was detected in three metastatic endometrial carcinomas, but not in the patient-matched surrounding normal tissues or in a malignant smooth muscle tumor of the uterus. Additionally, the protease was not detected in primary sarcomas of various origins.

While using the monoclonal antibody with standard staining techniques, it was recently discovered that the target 80-kDa protease was uniformly located around the periphery of the cells. More intense staining was seen on the pseudopodia and the mmembrane ruffles. Use of surface biotinylation techniques confirmed the plasma membrane localization of the protease. The 80 kDa protease could not be washed from the membrane fraction of homogenized breast cancer cells with high concentrations of NaCl, KCl nor EDTA. However, the protease was extractable with detergents.

The elevated expression of the 80 kDa protease at the pseudopod tip is considered important for allowing cancer cells to locally disrupt the ECM and allow forward locomotion. ECMs are composed of collagens, glycoproteins (such as fibronectin, laminin, and entactin/nidogen), proteoglycans, and glycosaminoglycans. To efficiently degrade ECM, many hydrolytic enzymes are believed to work in concert. Removal of one component of the ECM by a specific enzyme makes the other ECM component(s) more available for degradation by other specific enzymes. It has been demonstrated that depletion of glycoproteins from the ECM by trypsin treatment is necessary for the maximal digestion of elastin and collagen. Another type of interaction between matrix-degrading enzymes is that one enzyme may serve as an activator for others and may trigger a digestion cascade. Plasmin appears to activate several members of the MMP family, including interstitial collagenase and stromelysin.

In view of the above, it is seen that expression of this integral membrane gelatinase could allow cancer cells an alternative to other previously described matrix-degrading enzymes for degradation of ECM in close proximity to their surfaces. The newly-discovered, unexpected properties of the 80-kDa protease provide a novel means for evaluating metastatic potential of breast tumors.

Isolation of the 80-kDa protease was achieved from cell conditioned medium of T47D cells by combining concentration of the medium with ammonium sulfate and affinity chromatography using immobilized anti-80-kDa protease mAb 21-9. The purified protease consisted of three immunologically related forms, including the major activity, a doublet around 80 kDa and two minor ones at 95- and 110-kDa in the nonreduced state. In addition, a putative degradation product of 40 kDa was sometimes observed. The reduced form of the 80-kDa protease could be a single polypeptide chain with slightly higher molecular mass than the non-reduced form. These isolated proteolytic activity corresponded to the polypeptides recognized by the mAb 21-9 as shown by Western blotting. MAb 21-9 did not bind to the reduced protease, indicating that the epitope was dependent on an intramolecular disulfide bond(s). By analogy with the epitope recognized by mAb 21-9, the proteolytic activities of these enzymes were sensitive to the reducing agents such as 2-mercapto-ethanol and dithiothreitol. These proteases are, however, stable under acidic pH conditions down to 2.4; their activities after acidic pH treatment were recovered by neutralization.

Several minor polypeptides were also co-purified from immunoaffinity column. Of these polypeptides, some could potentially have gelatinolytic activity but were not recognized by mAb 21-9. These activities could be other proteases or the degraded fragments of the 80-kDa protease, which still bear the active site but lose the epitope recognized by mAb 21-9. It is possible that the other polypeptides were co-purified from the immunoaffinity column because they formed a complex with the 80-kDa protease through binding to a common binding protein(s) such as a protease inhibitor (s). Several attempts to further compare the 110- and 95 kDa protease with the 80-kDa protease in terms of tryptic map failed due to the low expression of both proteases in breast cancer cells, the ratio between the 80-kDa and both 95- and 110-kDa proteases, and the instability of these proteases in final purification step. (Human milk may, however, provide an alternative source for study the 95- and 110-kDa proteases, since both proteases, but not the 80-kDa protease, were detected in human milk.)

Compositions of the invention comprise carriers containing therein a monoclonal antibody which binds selectively with an 80-kDa matrix-degrading proteinase having an average molecular weight of about 80 kDa, which is active in the presence of $Ca^2$, $Mg^{2+}$ and $Mn^{2+}$, is active over a pH range of 7.5 to 9.5, and degrades gelatin and type IV collagen. The compositions containing the monoclonal antibodies may be provided in a kit along with reagents for testing samples obtained on biopsy. Compositions containing the monoclonal antibodies of the invention may be applied fresh tissue from biopsy or to frozen sections, as taught herein.

Materials and Methods

Cell lines and Culture Condition: Human hormone-dependent breast cancer cell line, T47D, was maintained in modified IMEM (Biofluides, Rockville, Md.) supplemented with 5% fetal calf serum (GIBCO, New York, N.Y.). To isolate the 80-kDa protease, the monolayers of T47D cells were washed twice with phosphate-buffered saline and were cultured in the absence of serum, in IMEM supplemented with insulin/transferrin/selenium (Biofluid, Rockville, Md.).

The rat myeloma cell line YB2/0 was purchased from ATCC and maintained in modified IMEM (Biofluides, Rockville, Md.) supplemented with 20% fetal calf serum (GIBCO, New York, N.Y.). The hybridoma cell line 21-9 was maintained in DMEM (Biofluides, Rockville, Md.) supplemented with 10% Nu-serum IV (Collaborative Biochemical, Bedford, Mss.). To produce mAb without contamination of bovine immunoglobulin, hybridoma cell line 21-9 was adapted into Protein Free Hybridoma Medium II (GIBCO, New York, N.Y.).

Tissue samples and tissue preparation: Frozen surgical specimens were obtained from Histopathology & Tissues Shared Resource of the Lombardi Cancer Center at Georgetown University Medical Center. Fresh tissue specimens were frozen in liquid nitrogen, gound by mortar and pestle, and extracted by radioiimmunoprecipitation assay (RIPA) buffer (150 mM NaCl, 1.0% Nonidet P-40, 0.5% deoxycholic acid, 0.1% SDS, and 50 mM Tris-HCl, pH 8.0) containing protease inhibitors (1.3 mM EDTA, 1 mM phenylmethylsulfonyl fluoride, 1 $\mu$M leupeptin). Protein concentration was determined using BCA Protein Assay Reagent obtained from Pierce of Rockford, Ill.

Preparation of 80-kDa protease as an immunogen: Partially purified 80-kDa protease was prepared as previously described (1) with some modification. Briefly, T47D cell conditioned serum-free media were collected and cellular debris were removed by centrifugation. Ammonium sulfate powder was added to the supernatant with continuous mixing to 65% saturation and sat in cold room overnight. The protein precipitates were obtained by centrifugation at 5,000×g for 20 min., and then dissolved in PBS. The 80-kDa protease was first separated from the major contaminating protein, transferrin, using hydroxyl-apetide chromatography (HTP, BioRad, Melville, N.Y.). To do so, the 80-kDa protease was first dialyzed against 10 mM phosphate (pH 6.8), and then applied to HTP column equilibrated with 10 mM phosphate (pH 6.8). The column was washed with the same solution. The transferrin was eluted by 40 mM phosphate (pH 6.8), and then the 80-kDa protease was eluted by 150 mM phosphate (pH 6.8). The protease was further subjected to gel filtration through a Sephacyl S-200 HR column (HiPrep 16/60, Pharmacia-LKB, Piscataway, N.J.) equilibrated with PBS. The column was eluted with the same buffer and the positive fractions were collected. The 80-kDa protease obtained by gel filtration was then precipitated by ammonium sulfate as described above, dialyzed against 20 mM Tris-HCl (pH 8.0), and applied onto a DEAE Sepharose FF column (Pharmacia-LKB, Piscataway, N.J.) which was equilibrated with 20 mM Tris-HCl (pH 8.0). The column was washed with equilibration buffer. The 80-kDa protease was eluted with a linear gradient from 0–0.4 M NaCl in DEAE equilibration buffer. The enzymatic activity of 80-kDa protease was assessed by gelatin zymography.

Monoclonal antibody production: Eight-week-old female Sprague-Dawley rats were immunized at two-week intervals with 20 g of proteins including the 80 kDa protease obtained from DEAE fractions. The immune response against the 80-kDa protease was tested by precipitation of the 80-kDa protease using the anti-sera obtained from rats. The spleenocytes from an immuno-positive rat were used to generated hybridoma according to a previously described method. Immunoblot analysis was applied in the primary screening. The positive hybridomas were subjected to secondary screening by their ability to precipitate the gelatinase activity of the 80-kDa protease.

Immunoprecipitation using rat antiserum: Fifteen $\mu$l of packed protein A-Sepharose (Pharmacia-LKB, Piscataway, N.J.) was incubated with 20 μg of affinity purified rabbit anti-rat IgG (Rockland, Gilbertsville, P.A.) and 50 μl of the antiserum at 4° C. overnight. The beads were washed 3 times with PBS. The 80-kDa protease obtained from DEAE chromatography was incubated with the antibody coated beads for 2 h at 4° C. Following centrifugation at low speed, supernatants were collected and the beads were washed 4 times with PBS containing 1% Triton X-100. The bound proteins were eluted with 2× SDS sample buffer without reducing agents at 37° C. for 5 min. and the SDS solubilized samples were analyzed by gelatin zymography.

Hybridoma screening bv Western blot analysis: To perform immunoblot screening, the 80-kDa protease was first resolved by 7.5% SDS polyacrylamide gel (mini gel 8×9 cm), and then transferred to nitrocellulose membranes. After blocking using 6% milk in PBS, each nitrocellulose membrane was cut into about 50 strips (1.6 mm in width). The cell conditioned media (100 1) from successful hybridomas were overlaid on nitrocellulose strips at room temperature for 2 hr. The nitrocellulose strips were washed with 1% Triton X-100 in PBS. The immunoreactive polypeptides were visualized using peroxidase-labelled anti-rat IgG antibody and the ECL detection system (Amersham Corp., Arlington Heights, Ill.).

Immunoblotting: Proteins were separated by 10% SDS-polyacrylamide gel electrophoresis, transferred overnight to nitrocellulose sheets (Schleicher & Schuell, Keene, N.H.) by diffusion, and subsequently probed with mAbs. Blots were incubated with mAb 21-9 diluted in PBS containing 1% BSA for 1 h at room temperature, and immuno-reactive polypeptides were visualized using the ECL detection system (Amersham Corp., Arlington Heights, Ill.).

Gelatin zymography: Gelatin zymography was conducted as previously described by Shi, et al. (*Cancer Res.* 53: 1409–1415 (1993)). Protease substrates utilized were gelatin (1 mg/ml). The electrophoresis was performed at a constant current of 15 mA. The gelatin gel was washed 3 times with PBS containing 2% Triton X-100 and incubated in PBS without any metal ions at 37° C. overnight.

Immobilization of monoclonal antibody on Sepharose 4B: Monoclonal antibody was isolated from protein-free cell conditioned medium using DEAE chromatography. Immunoaffinity beads were made by coupling 5 mg of mAb per ml of CNBr-activated Sepharose 4B as specified in the manufacture's instructions (Pharmacia-LKB, Piscataway, N.J.). The beads were washed with 0.1 M glycine-HCl (pH 2.4) before use.

Immunoprecipitation: Twenty five μl of packed mAb 21-9-Sepharose beads were incubated with 400 μl of the 80-kDa protease for 2 h at 4° C. Followed by centrifugation at low speed, the resulting supernatants were collected and the beads were washed 4 times with 1% Triton X-100 in PBS. The bound proteins were eluted with 30 μl of 0.1 M glycine-HCl (pH 2.4) and immediately neutralized by 2 M Trizma base. Five continuous elutions were performed.

Immunoaffinity chromatography: The immuno-affinity matrix was equilibrated with PBS containing 1% Triton X-100. The 80-kDa protease was loaded onto 1 ml column at the flow rate of 7 ml per hour. The column was washed with 1% Triton in PBS. Bound protease was then eluted using 0.1 M glycine-HCl (pH 2.4). Fractions were immediately neutralized using 2 M Trizma base.

Subcellular fractionation: T47D cells were washed with PBS three times and were swelled in 20 mM Tris-HCl (pH 7.4). The cells were scraped and homogenized with Dounce's homogenizer. The homogenates were then centrifuged at 600×g for 10 min. The pellets were referred as nuclear fraction. The resultant supernatant was centrifuged at 20,000×g for 20 min. The pellets were referred as membrane fraction and the supernatant as cytosol fraction. Although additional membrane pellets could be obtained from the cytosol fraction by 100,000×g centrifugation, and these membrane pellets also contain the 80-kDa protease, the yields of membrane and the 80-kDa protease were too little.

Immunofluorescent staining: T47D cells were pre-fixed with 3.7% formaldehyde for 10 min. Cells with or without permeabilization were stained by an indirect immunofluorescent technique utilizing mAb 21-9 at room temperature for 20 min., followed by fluorescein conjugated secondary antibody (Sigma, St. Louis, Mo.) for 20 min. at room temperature. Control cells were stained in the absence of primary antibody.

Surface biotinylation: Sulfosuccinimidobiotin (sulfo-NHS-Biotin, Pierce) or Sulfosuccinimidyl 6-(biotinamido) Hexanoate (NHS-LC-Biotin, Pierce) was used to label the cell surfaces. To label cell surfaces with biotinylation reagents, confluent T47D cells grown in 15 cm dishes were washed with PBS three times, and then sulfo-NHS-Biotin or NHS-LC-Biotin (2 mg in 10 ml of PBS per dish) was added. Cells were incubated at room temperature for 20 min. After incubation, cells were washed with 50 mM Tris-HCl (pH 7.4) and 150 mM NaCl three times. Biotinylated cells were then subjected to subcellular fractionation and the membrane fractions were collected.

Expression analysis of the 80 kDa protease in mammary tissues: Samples of proteins were extracted by RIPA buffer from normal breast tissue surrounding the breast tumor of five different patients, an abnormal breast of hypertrophy, a normal breast tissue of non-cancerous health breast from a breast cancer patient and tumors of ten different patients. Proteins were separated by SDS-PAGE, transferred to membrane and probed by mAb 21-9. The positions of the 80 kDa protease and both 95 and 110 kDa protease complexes were indicated according to the sample of T-47D cells.

Human immunoglobulin was the major false signal in almost every sample. This could be significantly reduced by incubating with protein A-Sepharose beads prior to SDS-PAGE.

Expression analysis of the 80 kDa protease in gynecological tumors: Samples of proteins were extracted by RIPA buffer from two ovarian carcinomas, three endometrial carcinomas, three patient-matched normal tissues surrounding tumors, an ovarian carcinoma which is diffucilt to classify, a muncinous tumor with low maligant potential, three stomal derived tumors, including a granulosa cell tumor and two fibrothecomas. Proteins were separated by SDS-PAGE, transferred to PVDF membranw and probed with mAb 21-9. The positions of the 80 kDa protease and both 95 and 110 kDa protease complexes were indicated according to the sample of T-47D cells. Human immunogiobuline was again the major false signal.

Expression analysis of the 80 kDa protease in ovarian carcinomas: Samples of proteins were extracted by RIPA buffer from ten ovarian carcinomas. These included four endometriod carcinomas, adenocarcinomas with metastases from colon primary and breast primary malignancies, one clear cell carcinoma, two papillary serous carcinomas and one mucinous cystadenocarcinoma. Proteins (100 μg per well) were separated by SDS-PAGE, transferred to PVDF membrane and probed with mAb 21-9. The positions of the 80 kDa protease and both 95 and 110 kDa protease complexes were indicated according to the sample of T-47D cells. There was no 80 kDa protease detected in any human carcinoma examined. There were several minor false signals due to the longer exposure to X-ray film. Human immunoglobulin was again the major false signal in the cell extracts.

Amino acid composition analysis: Immunoaffinity purified 80-kDa protease was precipitated by addition of one tenth of the sample volume of the 100% trichloroic acid (TCA) and washed with cold ethanol three times. The 80-kDa protease was subjected to SDS-PAGE (7.5% acrylamide) and then transferred onto poly(vinylidene fluoride) membrane (Bio-Rad). The 80-kDa was visualized by Coomassie Blue staining and excised for amino acid composition analysis. To do so, bands were cut from blot, and a section, equal to the sample band size was cut from the edge of the blot to use as a control. The cut bands were placed in a 6×50 mm Pyrex tube. One hundred microliters of 6 N HCL was added to each tube, then the samples were vapor hydrolyzed for 18 minutes in using a CEM Microwave digestion system. The bands were washed three times with 0.1 N HCl, 20% methanol. The rinses were combined and dried on a Heto speed vac. The samples were pre-column derivitized with PITC (phen-ylisothiocyanate), and run on reverse phase HPLC. The HPLC system was comprised of Waters M6000 pumps, 680 gradient controller, 440 UV detector.

The results were analyzed on a waters maxima software system. The separation was performed with a Water's free amino acid column (3.9×300 mm). Column temperature was 38° C.

Monoclonal antibody production: In order to further characterize the 80-kDa protease which had previously been identified in human breast cancer cells, a monoclonal antibody was generated (mAb) which was directed against this protease. Since partially purified 80-kDa protease was used as an immunogen, a hybridoma library was screened by Western blot analysis to select mabs which recognized polypeptides of approximately 80 kDa. The selected hybridoma lines were subcloned and further tested for their ability to precipitate the 80-kDa protease.

An immuno-positive rat whose serum contained antibodies against the 80-kDa protease was sacrificed and its spleen cells were fused with rat myeloma cells YB2/0. Successful hybridomas were screened by immunoblot analysis. One hybridoma line (mAb 21-9) was selected, subcloned and further characterized. To verify that mAb 21-9 (IgGl) directed against the 80-kDa protease, immunoprecipitation was performed. The gelatinase activity of the 80-kDa protease as well as its corresponding polypeptide were completely depleted by mAb 21-9. The absorbed protease could be eluted from beads by 0.1 M glycine-HCl (pH 2.4). The enzymatic activity of the 80-kDa protease remained active after neutralizing the low pH eluate with 2 M Trizma base. The 80-kDa protease appears to readily undergo degradation. An apparently degraded form at 40 kDa was also precipitated by mAb 21-9 and its corresponding polypeptide was also recognized by mAb 21-9 by immunoblotting analysis suggesting the active site of the 80 kDa protease and the epitope recognized by mAb 21-9 were both on the 40 kDa fragment.

One-step purification of the 80-kDa protease using immunoaffinity chromatography—The results obtained from immunoprecipitation suggested that the 21-9 mAb was competent for immunoaffinity purification of the 80-kDa protease. The 80-kDa protease was concentrated from cell conditioned medium by addition of ammonium sulfate to 65% saturation, and then the precipitated proteins were dialyzed against PBS. The immunoaffinity chromatography was carried out by applying concentrated medium onto a 1 ml of a mAb 21-9-Sepharose column. The protease was eluted by 0.1 M glycine-HCL (pH 2.4), and the eluate was subjected to three assays, including SDS-PAGE to examine the purity, gelatin zymography to assess its proteolytic activity, and immunoblot analysis to check its immunological reactivity. The 80-kDa protease could easily be isolated to near homogeneity by immunoaffinity purification from the cell conditioned medium. Approximately 2 µg of the 80-kDa protease were obtained from a liter of cell conditioned medium which contained approximately 40 mg of protein. It represented at least ten thousand folds increase in the purity by this onestep purification. The recovery rate of protease was estimated at greater than 50% based on zymography. In addition, several minor polypeptides were co-purified, including 110-, and 95-kDa polypeptides. While the 80-kDa protease could be eluted from an immunoaffinity column by glycine-HCl (pH 2.4), its proteolytic activity could also be recovered by neutralization as determined by gelatin zymography. In addition to the 80-kDa protease, several weak gelatinolytic activities were seen on gelatin zymograms. The 110- and 95-kDa activities corresponded in size to the two polypeptides seen on SDS-gels. The immunological relationships between the 80-kDa protease and these two, 110- and 95-kDa polypeptides were verified by Western blotting analysis using mAb 21-9. Both 110- and 95-kDa bore the epitope which was recognized by anti-80-kDa protease, suggesting that they were directly captured by mAb 21-9 during immunoaffinity column chromatography. Taken together, the 110- and 95-kDa gelatinases were closely related to the 80-kDa protease; probably the proform of the 80-kDa protease. Utilizing the mAb 21-9, the 80-kDa protease could easily and quantitatively be purified.

Besides the differences in biochemical characteristics such as gelatin binding site, the electrophoretic mobility, and inhibitor profile as described in the Introduction, the amino acid composition of the 80-kDa protease was compared with those of gelatinase A (72 kDa) and gelatinase B (92 kDa). There was no similarity between the 80-kDa protease and the other two gelatinases in their amino acid composition.

Plasma membrane localization of the 80-kDa protease: Although the 80-kDa protease was initially identified and purified from the cell conditioned medium, the protease was associated with membrane fraction when the T47D cells were subjected to subcellular fractionation. For subcellular fractionation, the cells were swollen in hypotonic buffer and the nuclei were separated by low speed centrifugation. The resultant supernatant was further fractionated into a membrane fraction and cytosol fraction by high speed centrifugation. The association of the 80-kDa protease to membrane fractions was sufficiently strong that it resisted salt washes with 1 M NaCl and 2 M KCl as well as 0.1 M EDTA. However, it could be extracted by detergents. These results suggested that the association of the 80-kDa protease to the membrane was extremely strong and that the protease did not maintain this interaction through a loose association with other membrane-bound proteins nor attached via metal ions. We propose that the 80-kDa protease could be an integral membrane protein. In addition, there was no prominent difference in the size of the 80-kDa protease comparing the membrane-bound and the secreted forms. The 95-, 110-kDa and the 40-kDa putative degraded product were indistinctly seen in the membrane fraction. The ratios of the 80-kDa to 95- and 110-kDa forms in the membrane fraction appeared to be similar to the ratios in the cell conditioned medium.

To examine more precisely the subcellular localization of the 80 kDa protease, T47D cells were grown on glass coverslips, fixed with or without permeablization by detergent, and labeled with the anti-80-kDa protease mAb 21-9. MAb 21-9 stained the surfaces of both non-permeablized and permeablized cells most intensively at the membrane ruffles. The 80-kDa protease was also localized in intracellular compartments after cells were permeablized with 0.5% Triton X-100. The fact that the 80-kDa protease is specifically expressed on the cell surface was further verified with a surface biotinylation technique in which the surface proteins of T47D cells were biotinylated by sulfo-NHS-biotin or NHS-LC-biotin. These two protein modification reagents are water soluble and not permeant to the plasma membrane; thus, biotinylation is restricted to the cell surface. After surface biotinylation, the membrane fractions were collected and the Triton X-100 extraction was carried out using the membrane fractions. The total cellular 80-kDa protease pool, including the biotinylated surface portion, was then specifically precipitated using mAb 21-9-Sepharose beads and the total biotinylated cell surface proteins and the surface biotinylated 80-kDa protease was detected by peroxidase-labeled streptavidin. These results strongly suggested that a portion of the 80-kDa protease pool is expressed on the cell surface.

We claim:

1. A composition of matter comprising the monoclonal antibody 21-9 in a carrier.

2. A monoclonal antibody 21-9.

3. A composition of claim 1 containing, additionally, breast tissue.

4. A composition of claim 3 containing, additionally, a second antibody.

5. A composition of claim 4 wherein the second antibody is fluorescein-conjugated antibody.

6. A composition of claim 1 wherein the antibody is bound to a non-reduced protease.

7. A composition of claim 1 which is on an immunoaffinity column.

8. A composition of claim 3 wherein the tissue is in the form of fresh tissue.

9. A composition of claim 3 wherein the tissue is in the form of frozen sections.

* * * * *